(12) United States Patent
Slayton et al.

(10) Patent No.: US 6,440,071 B1
(45) Date of Patent: Aug. 27, 2002

(54) PERIPHERAL ULTRASOUND IMAGING SYSTEM

(75) Inventors: Michael H. Slayton, Tempe; Peter G. Barthe, Phoenix; Paul Jaeger, Mesa; Vadim Kouklev, Tempe, all of AZ (US)

(73) Assignee: Guided Therapy Systems, Inc., Mesa, AZ (US)

( * ) Notice: Subject to any disclaimer, the term of this patent is extended or adjusted under 35 U.S.C. 154(b) by 0 days.

(21) Appl. No.: 09/419,543

(22) Filed: Oct. 18, 1999

(51) Int. Cl.$^7$ ................................................. A61B 8/00
(52) U.S. Cl. ........................................ 600/437; 128/916
(58) Field of Search ................................. 600/437–447, 600/407; 128/916, 903, 904, 922; 382/128, 132; 341/65; 395/705; 705/3; 378/114

(56) References Cited

U.S. PATENT DOCUMENTS

| | | | | |
|---|---|---|---|---|
| 5,321,520 A | * | 6/1994 | Inga et al. | 358/403 |
| 5,603,323 A | * | 2/1997 | Pflugrath et al. | 128/903 |
| 5,715,823 A | * | 2/1998 | Wood et al. | 600/437 |
| 5,795,297 A | * | 8/1998 | Daigle | 600/447 |
| 5,853,367 A | * | 12/1998 | Chalek et al. | 128/916 |
| 6,101,407 A | * | 8/2000 | Groezinger | 128/922 |
| 6,159,150 A | * | 12/2000 | Yale et al. | 600/437 |
| 6,171,244 B1 | * | 1/2001 | Finger et al. | 600/437 |
| 6,210,327 B1 | * | 4/2001 | Brackett et al. | 600/407 |
| 6,287,257 B1 | * | 9/2001 | Matichuk | 600/437 |
| 6,325,540 B1 | * | 12/2001 | Lounsberry et al. | 378/114 |
| 6,356,780 B1 | * | 3/2002 | Licato et al. | 382/128 |

* cited by examiner

Primary Examiner—Francis J. Jaworski
Assistant Examiner—Ali M. Imam
(74) Attorney, Agent, or Firm—Snell & Wilmer, L.L.P.

(57) ABSTRACT

A peripheral ultrasound imaging system for connection to a personal computing device or a computer network which enables real time ultrasound imaging without additional modules and without the need to modify, augment or replace the existing central processing unit. The peripheral ultrasound imaging system includes an ultrasound probe, an electronic apparatus capable of sending and receiving signals to and from the ultrasound probe, a hardware link connecting the electronic apparatus to a personal computer or computer network, and a software program for controlling the ultrasound probe, the electronic apparatus, and the hardware link. The ultrasound probe is connected to the electronic apparatus and the electronic apparatus is in turn connected to a personal computing device or a computer network.

17 Claims, 5 Drawing Sheets

PERIPHERAL ULTRASOUND IMAGING SYSTEM

FIELD OF THE INVENTION

The present invention relates generally to a peripheral ultrasound imaging system. More particularly, the present invention relates to a peripheral ultrasound imaging system capable of connection to a personal computing device or a computer network that enables a user to perform real time ultrasound imaging without the need for a plurality of modules typically needed for ultrasound imaging, such as, for example, scanning modules, display modules and converter modules, and without the need to modify, augment or replace the central processing unit of the personal computing device or computer network.

BACKGROUND OF THE INVENTION

As the capability and speed of central processing units (CPUs) continue to increase, CPUs will become capable of being utilized for performing a number of applications using specialized peripheral devices or equipment that previously were used in conjunction with specialized processors specifically tailored for use with the specialized peripheral devices or equipment. The medical field is one area where the CPUs of personal computing devices and computing networks may be utilized for carrying out methods and procedures requiring specialized devices or equipment which previously required tailored processors.

One example of using the processors of commercially available personal computers for carrying out a medical diagnostic procedure is disclosed in U.S. Pat. No. 5,795,297 issued to Daigle. This patent describes an ultrasonic diagnostic imaging system with a personal computer platform which processes digital echo signals and produces ultrasonic image signals for display. However, the ultrasound imaging system disclosed in Daigle requires manipulation and adjustment of the CPU components of the personal computer platform by plugging an expansion bus board into one of the motherboard's expansion bus sockets contained in the CPU. In addition, several cards such as a DSP card, a network card, and a video card are connected to the expansion bus board. This type of ultrasound imaging system does not allow for easy connection of an ultrasound probe to a personal computer for performing ultrasound imaging.

Accordingly, there is a need for an efficient and easy to use peripheral device or system that connects to a personal computing device for performing ultrasound imaging as well as other possible medical diagnostic and therapeutic processes. Furthermore, there is a need for a compact, efficient and easy to use peripheral device or system that can be directly connected to a computer network for performing diagnostic and therapeutic medical processes such as, for example, ultrasound imaging and therapy.

BRIEF SUMMARY OF THE INVENTION

It is a principal object of the present invention to provide a peripheral ultrasound imaging system that can be easily connected to a personal computing device or computer network for performing ultrasound imaging and/or ultrasound therapy.

It is another object of the present invention to provide a peripheral ultrasound imaging system that utilizes software that may reside in part or in whole in either the peripheral ultrasound imaging system itself or a personal computer or computer network storage device.

It is still another object of the present invention to provide a peripheral ultrasound imaging system that utilize a variety of ultrasound probes including, but not limited to, a motorized annular array probe, a motorized single element probe, a motorized multiple focus single element probe, and a transducer array.

It is yet another object of the present invention to provide a peripheral ultrasound imaging system that is efficient and cost effective in that it does not require any manipulation or adjustment of the CPU components of an existing personal computer or computer network for use with the personal computer or computer network.

The above and other aspects of the present invention may be carried out in one form by a peripheral ultrasound imaging system which includes an ultrasound probe, an electronic apparatus connected to the ultrasound probe that comprises components for sending and receiving signals to and form the ultrasound probe, a hardware link connecting the electronic apparatus to an existing computing device or computer network, and a software program for controlling the ultrasound probe, the electronic apparatus, and the hardware link.

BRIEF DESCRIPTION OF THE DRAWINGS

A more complete understanding of the present invention may be derived by referring to the detailed description and claims when considered in connection with the following illustrative Figures. In the following Figures, like reference numbers refer to similar elements throughout the Figures.

DETAILED DESCRIPTION OF EXEMPLARY EMBODIMENTS

The subject invention relates to a peripheral ultrasound imaging system that can be connected directly to a personal computing device or a computer network. The peripheral ultrasound imaging system includes an ultrasound probe, an electronic apparatus, a hardware link, and a software system, all of which enable a user to perform real time ultrasound imaging without the need for the plurality of modules typically required for ultrasound imaging such as front end modules for controlling transmission and responding to reception by the ultrasound probe for various types of scanning, scan converter modules, display modules and recorder modules. In addition, the peripheral ultrasound imaging system of the present invention enables a user to perform ultrasound imaging with an ultrasound probe without the need to modify, augment or replace the central processing unit of a personal computer workstation or computer network.

The present invention may be described herein in terms of functional block components and various processing steps. It should be appreciated that such functional blocks may be realized by any number of hardware components configured to perform the specified functions. For example, the present invention may employ various integrated circuit components, e.g., memory elements, digital signal processing elements, logic elements, look-up tables, and the like, which may carry out a variety of functions under the control of one or more microprocessors or other control devices. In addition, those skilled in the art will appreciate that the present invention may be practiced in conjunction with any number of data transmission protocols and that the systems described herein are merely exemplary applications for the invention. Further, it should be noted that the present invention may employ any number of conventional techniques for data transmission, signaling, data processing, network control, and the like. Such general techniques that may be known to those skilled in the art are not described in detail herein.

It should be appreciated that the particular implementations shown and described herein are illustrative of the invention and its best mode and are not intended to otherwise limit the scope of the present invention in any way. Indeed, for the sake of brevity, conventional signal processing, data transmission, and other functional aspects of the systems (and components of the individual operating components of the systems) may not be described in detail herein. Furthermore, the connecting lines shown in the various figures contained herein are intended to represent exemplary functional relationships and/or physical couplings between the various elements. It should be noted that many alternative or additional functional relationships or physical connections may be present in a practical communication system.

Figure 1:
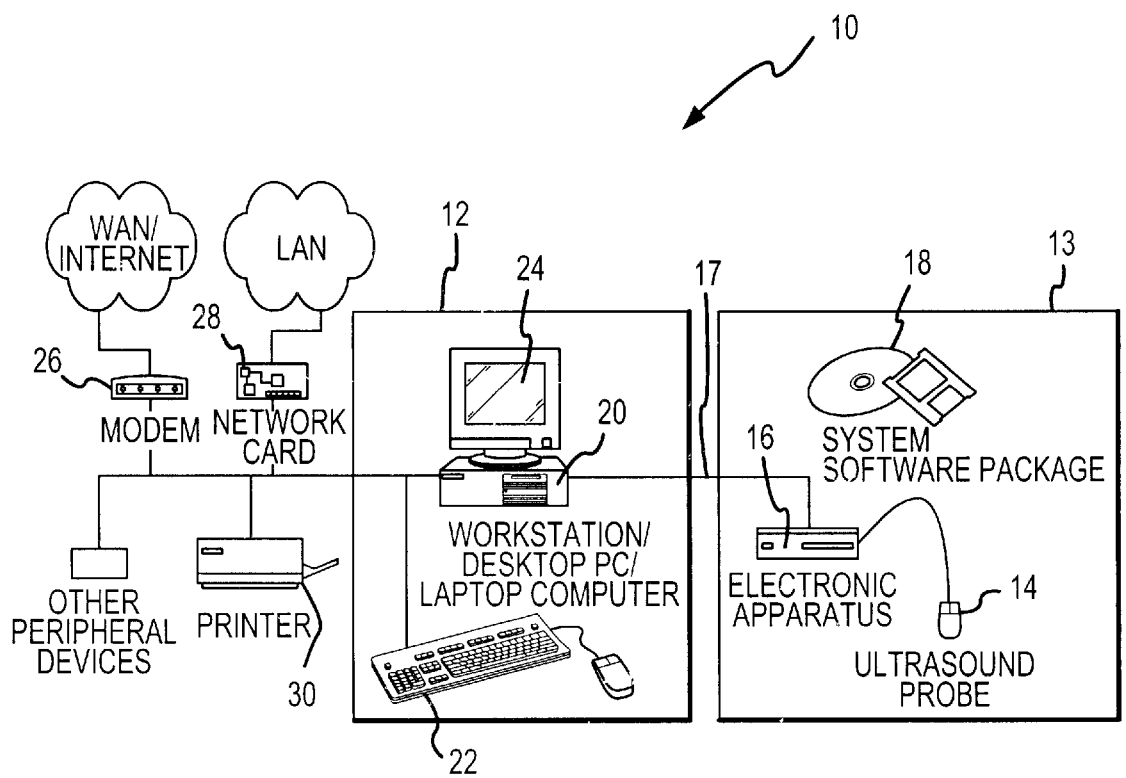
FIG. 1 is a schematic of one exemplary embodiment of an ultrasound imaging arrangement using the peripheral ultrasound imaging system of the present invention.

Turning now to FIG. 1, there is shown a schematic of one exemplary embodiment of an ultrasound imaging arrangement using the peripheral ultrasound imaging system of the present invention. The ultrasound imaging arrangement 10 shown in FIG. 1 includes a personal computing device 12, such as a desktop personal computer (PC), laptop computer, or hand held computer, that is connected to the peripheral ultrasound imaging system 13 of the present invention. The peripheral ultrasound imaging system 13 includes an ultrasound probe 14 for application to an area of interest of a patient, an electronic apparatus 16 for sending and receiving signals to and from the ultrasound probe 14, a hardware link 17 connecting the electronic apparatus 16 to the personal computer workstation 12, and a software program 18 for controlling the ultrasound probe 14, the electronic apparatus 16, and the hardware link 17. It should also be noted that the hardware link 17 may comprise a wireless link. The personal computer workstation 12 should include a central processing unit 20, means for inputting information into the central processing unit such as a keyboard 22 or touch screen capability on the screen of a display monitor, and a means for displaying images such as a monitor 24. One or more additional hardware devices may also be connected to the personal computer workstation 12 such as, for example, a modem 26 for connecting to an internet, a network card 28 for connecting to a local area network, or printer 30 for providing hard copies of images displayed on the monitor 24. The present invention also contemplates the inclusion of any other hardware devices which can be easily connected to the personal computer workstation 12.

Figure 2:
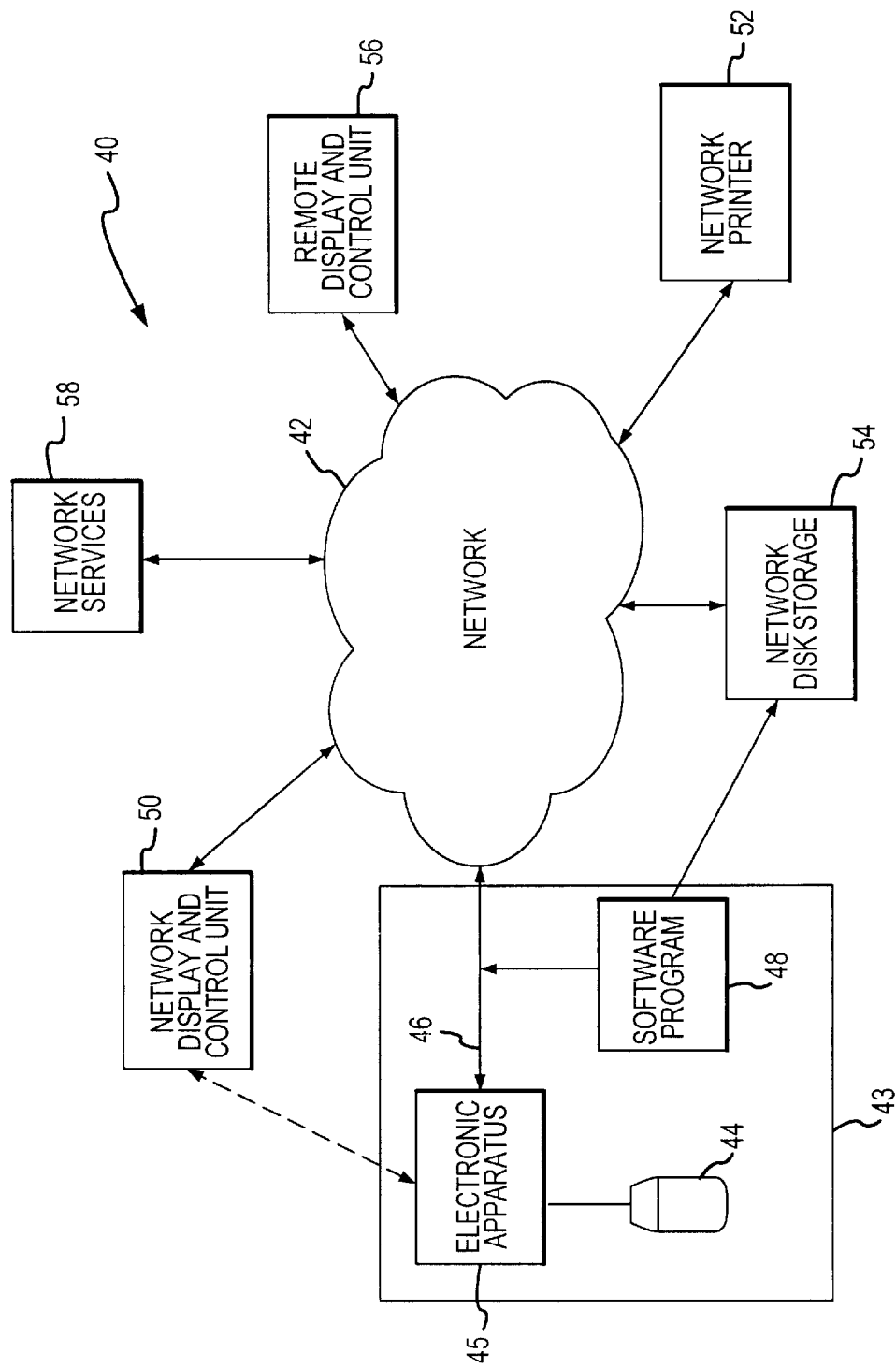
FIG. 2 is a schematic of another exemplary embodiment of an ultrasound imaging arrangement using the peripheral ultrasound imaging system of the present invention.

A schematic of another exemplary embodiment of an ultrasound imaging arrangement using the peripheral ultrasound imaging system of the present invention is shown in FIG. 2. FIG. 2 illustrates an ultrasound imaging arrangement 40 which includes a computer network 42 such as, for example, the internet, and the peripheral ultrasound imaging system 43 of the present invention. The peripheral ultrasound imaging system 43 of the present invention includes an ultrasound probe 44 for application to an area of interest of a patient, an electronic apparatus 45 for sending signals to, and receiving signals from, the ultrasound probe 44, a hardware link 46 for connecting the electronic apparatus 45 to the computer network 42, and a software program 48 for controlling the ultrasound probe 44, the electronic apparatus 45, and the hardware link 46. Once again, it should be noted that the hardware link 46 may form a wireless connection. The ultrasound imaging arrangement 40 also includes a networked display and control unit 50 for displaying and controlling information, data and images associated with the electronic apparatus 45. For example, the networked display and control unit 50 may be a PC with a browser, or a personal digital assistant, or any other type of device with control and display abilities for controlling the electronic apparatus 45 and displaying information from the electronic apparatus 45. Alternatively, the networked display and control unit 50 may just comprise display capabilities for displaying information and images from the electronic apparatus 45 while the electronic apparatus 45 itself comprises user control ability. With respect to this second exemplary embodiment of an ultrasound imaging arrangement using the peripheral ultrasound imaging system 43 of the present invention, no PC is needed and the electronic apparatus 45 is connected directly to the computer network 42. However, in addition to the previous listed components, the ultrasound imaging arrangement 40 of the present invention may further include one or more additional hardware devices connected directly to the computer network 42 such as, for example, a network printer 52 for providing hard copies of the information and images displayed on the networked display and control unit 50, a network disk storage device 54 for storing information, software programs, data and images from the electronic apparatus 45 and the computer network 42, a remote display and control unit 56 for enabling a user to function remotely from the ultrasound application site, and a network services device 58 for providing network support and new software to the computer network 42.

It will be understood by those skilled in the art that the software program 48 for controlling the electronic apparatus 45 may reside in part or in whole within electronic apparatus 45 or network storage device 54.

Figure 3:
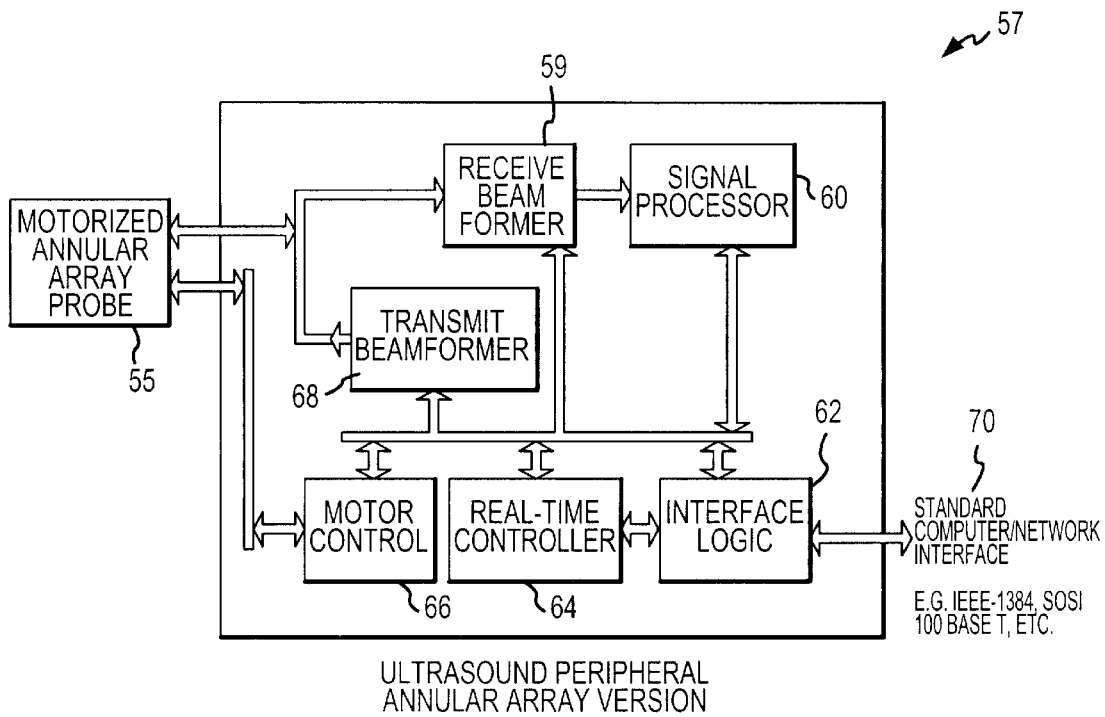
FIG. 3 is a block diagram of a first exemplary embodiment of the hardware link of the present invention for connecting an ultrasound probe to a personal computer workstation or computer network.

The electronic apparatus 16,45 of the peripheral ultrasound imaging system of the present invention may comprise several configurations. FIG. 3 shows a block diagram of a first exemplary embodiment of the electronic apparatus of the present invention for sending signals to and from the ultrasound probe 55 where the ultrasound probe 55 is a motorized annular array probe. The electronic apparatus 57 includes a beamformer receiver 59 for receiving signals from the motorized annular array probe 55, a signal processor 60 for processing signals from the beamformer receiver 59, an interface logic 62, a real-time controller 64, a motor controller 66, and a beamformer transmitter 68.

The interface logic 62 communicates with the signal processor 60, the real-time controller 64, the beamformer receiver 59, the beamformer transmitter 68 and a standard computer/network interface 70, such as, for example, Institute of Electrical and Electronics Engineers Standard 1394 (IEEE-1394), the Small Computer System Interface (SCSI), 100 Base T, Fast Ethernet, and wireless RF modems. The real-time controller 64 is configured to communicate with the interface logic 62, the signal processor 60, the beamformer receiver 59, and the beamformer transmitter 68. The motor control 66 receives information from the signal processor 60, the interface logic 62 and the real-time controller 64 and in turn controls the motorized annular array probe 55 based on the information it receives. The beamformer transmitter 68 and the motor control 66 receive information from the real-time controller 64 and, based on the information received, transmit beamformer and motor control signals to the motorized annular array probe 55. Ultrasound echos received from the motorized annular array probe 55 and the beamformer receiver 59 are sent to the signal processor 60 and next to the interface logic 62.

Figure 4:
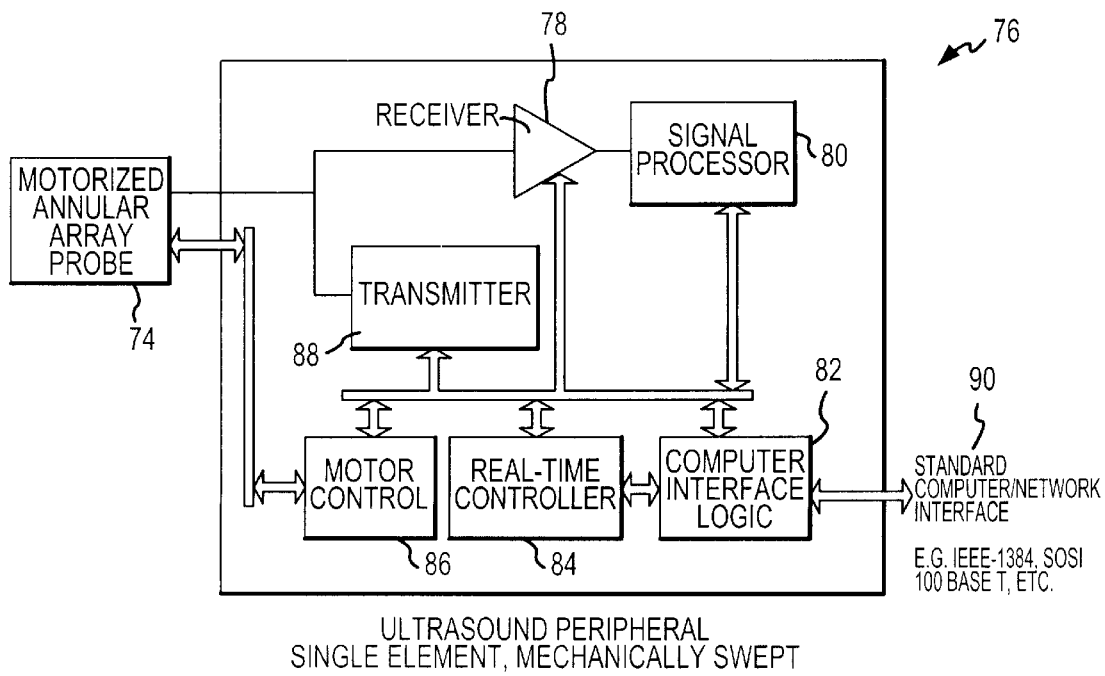
FIG. 4 is a block diagram of a second exemplary embodiment of the hardware link of the present invention for connecting an ultrasound probe to a personal computer workstation or computer network.

A second exemplary embodiment of the electronic apparatus and hardware link of the present invention for connecting a motorized single element ultrasound probe 74 to a personal computer workstation or computer network is shown in block diagram in FIG. 4. The single element ultrasound probe 74 could be a fixed-focus element or a multiple focus 1.25-D probe in which various focusing areas of the single element are switched ON and OFF at any given transmit-receive depth to produce a better focused image.

Like the electronic apparatus 56 for a motorized annular array probe 54 shown in FIG. 3, the electronic apparatus 76 for the motorized single element probe 74 includes a receiver 78, a signal processor 80, a computer interface logic 82, a real time controller 84, a motor control 86, and a transmitter 88. Aside from the fact that the receiver 78 and transmitter 88 are receiving and transmitting individual signals coming from the motorized single element probe 74, the configuration of the information flow through, and communication between, the components comprising the electronic apparatus 76 is substantially the same as that shown in FIG. 3 with respect to the electronic apparatus 56 that is connected to the motorized annular array probe 54.

Figure 5:
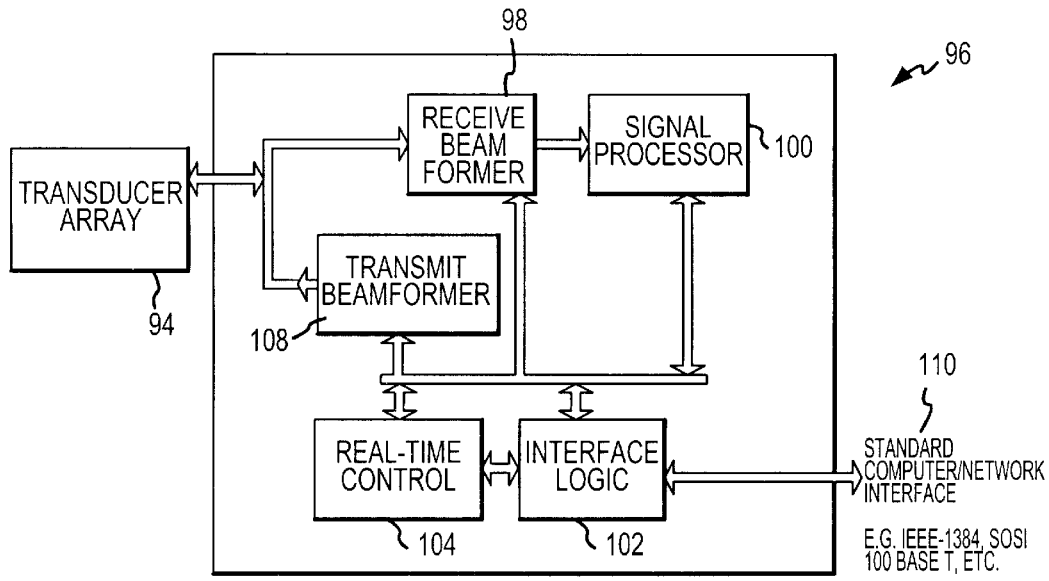
FIG. 5 is a block diagram of a third exemplary embodiment of the hardware link of the present invention for connecting an ultrasound probe to a personal computer workstation or computer network.
Figure 6:
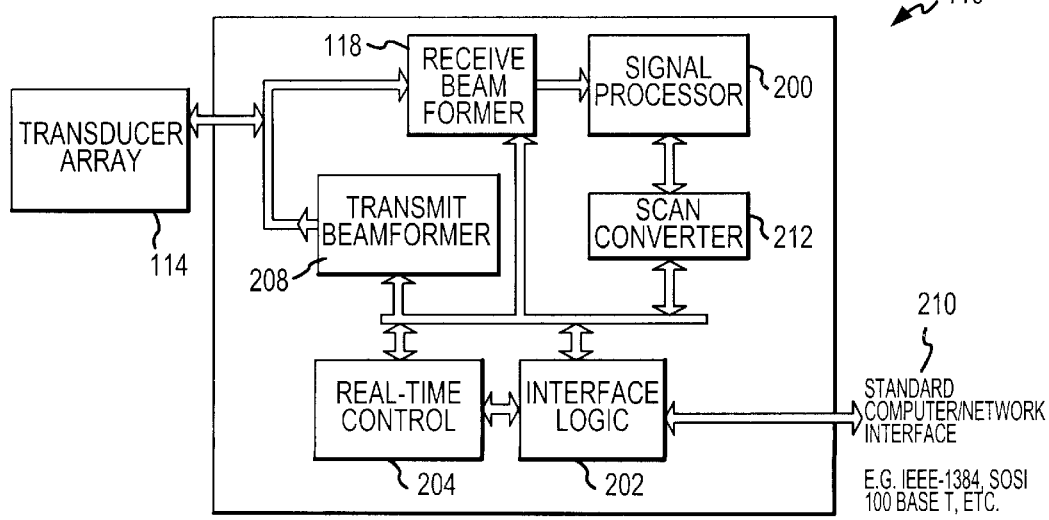
FIG. 6 is a block diagram of a fourth exemplary embodiment of the hardware link of the present invention for connecting an ultrasound probe to a personal computer workstation or computer network.

FIGS. 5 and 6 show block diagrams of third and fourth exemplary embodiments, respectively, of the electronic apparatus and hardware link of the present invention for connecting an ultrasound probe to a personal computer workstation or computer network. The third embodiment of the electronic apparatus 96 for connecting a transducer array 94 such as, for example, a curved, linear, or phased array ultrasound transducer, to a personal computer workstation or a computer network includes beamformer receiver 98 for receiving signals from the ultrasound transducer array 94, a signal processor 100 for processing signals received by the beamformer receiver 98, an interface logic 102, a real-time control 104 and a beamformer transmitter 108. The interface logic 102 communicates with the signal processor 100, the real-time control 104 and a standard computer/network interface 110 such as, for example, IEEE-1894, SCSI, 100 BaseT, Fast Ethernet, and wireless RF modems. The real-time control 104 communicates with the signal processor 100, the interface logic 102, the beamformer receiver 98 and the beamformer transmitter 108 to provide real-time information relating to the signals produced by the ultrasound transducer array 94. The beamformer transmitter 108 receives information from the signal processor 100, the interface logic 102, the real-time controller 104 and, based on the information received, transmits beamformer signals to the ultrasound transducer array 94 and returning ultrasound echos are received by the beamformer receiver 108.

The fourth embodiment of the peripheral hardware link 116 (See FIG. 6) for connecting a transducer array 114 such as, for example, a curved, linear, or phased array ultrasound transducer, to a personal computer workstation or a computer network includes the same elements as the electronic apparatus 94 shown in FIG. 5, namely a beamformer receiver 118, a signal processor 200, an interface logic 202, a real-time control 204, and a beamformer transmitter 208, with the addition of a scan converter 212 for receiving processed signals from the signal processor 200. The scan converter 212 communicates with the interface logic 202, the real-time control 204, the beamformer receiver 118 and the beamformer transmitter 208 to provide a real time image scan of the signals emitted from the ultrasound transducer array 114.

Figure 7:
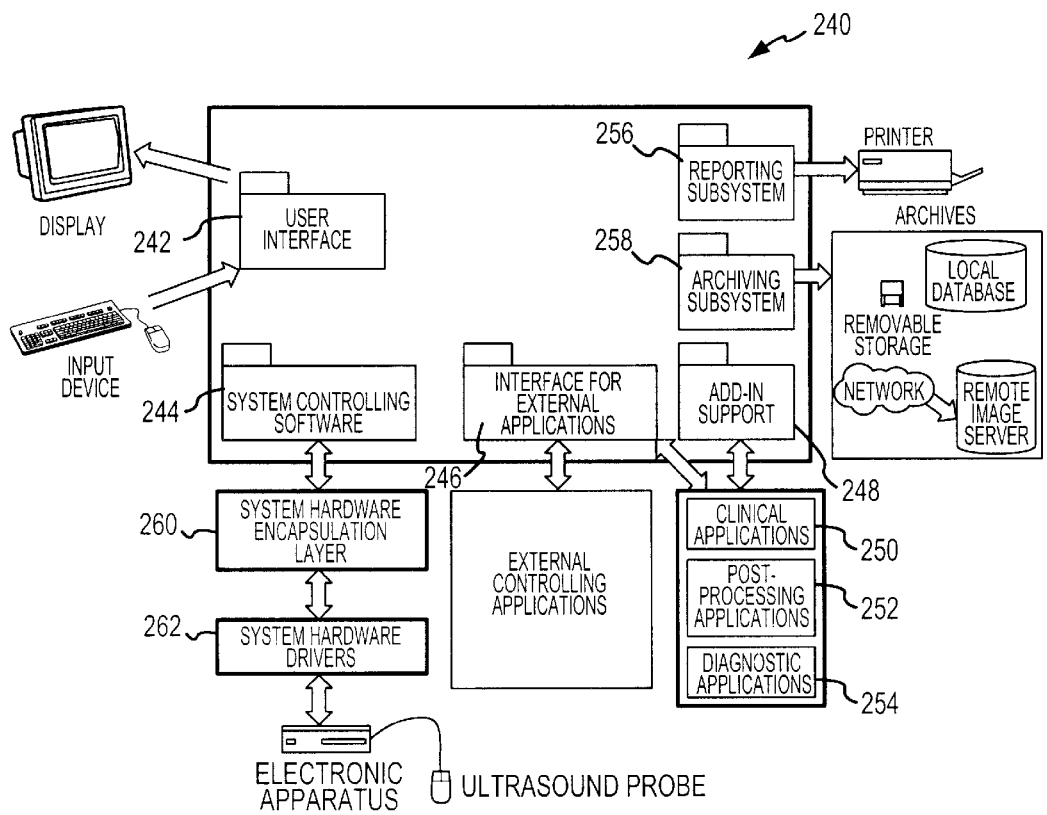
FIG. 7 is a block diagram of the software architecture used in the peripheral ultrasound imaging system of the present invention.

Turning now to the software program which comprises part of the peripheral ultrasound imaging system of the present invention, a block diagram of the software architecture used in the ultrasound imaging system of the present invention is shown in FIG. 7. The software architecture 240 which comprises a part of the peripheral ultrasound imaging system of the present invention includes a user interface 242 for providing a user with a means for interfacing with the peripheral ultrasound imaging system of the present invention through the electronic apparatus, a personal computer workstation, or a computer network, an ultrasound system control 244 for providing an interface for controlling the peripheral ultrasound imaging system of the present invention through a personal computer workstation, a computer network, the ultrasound probe, or the electronic apparatus, an external application interface 246 for providing an interface for an external application through a personal computer workstation, a computer network, the ultrasound probe, the electronic apparatus and the software program for controlling the electronic apparatus, and an add-in support application interface 248 for allowing external applications to be integrated into the peripheral ultrasound imaging system. Such external applications may include, for example, clinical applications 250 whereby ultrasound may be used in medical applications such as in for providing therapy, post-processing applications 252 such as cleaning noise from scanned images, and diagnostic applications 254 such as self-testing and diagnosis.

The software program 240 may also include a reporting application interface 256 for providing a user with a hard copy of any scanned images and a archiving application interface 258 for providing a user means for archiving information produced from the ultrasound imaging apparatus or information from a computer network. Finally, the peripheral ultrasound imaging system of the present invention may also include encapsulation layer software 260 for providing a stable interface between the software program 240 for controlling the electronic apparatus and each of the additional hardware elements comprising the ultrasound imaging arrangement including, but not limited to, a personal computer workstation, a computer network, the ultrasound probe, the electronic apparatus, the hardware link, and any additional hardware devices previously discussed with reference to the exemplary system embodiments shown in FIGS. 1 and 2. The encapsulation layer software 260 may comprise a set of logical device components for providing a high level interface to each of the hardware components contained within the ultrasound imaging arrangement using the peripheral ultrasound imaging system of the present invention. A separate interface must be designed for every device. The encapsulation layer software 260 may also include a control component which controls the way all logical device components communicate with one another. In addition, a plurality of hardware drivers 262 may be included for passing data between the hardware, namely the personal computer workstation, the computer network, the ultrasound probe, the electronic apparatus, the hardware link, and any additional hardware devices, and the encapsulation layer software 260.

It should be further understood by those skilled in the art that the peripheral ultrasound imaging system of the present invention can also be used for three dimensional (3-D) ultrasound imaging and/or 3-D ultrasound imaging, monitoring and therapy (imaging/monitoring/therapy). 3-D ultrasound imaging and/or 3-D ultrasound imaging/monitoring/therapy can be achieved by providing an electronic or mechanical means (such as a probe, electronic apparatus and hardware link of the present invention) of accessing multiple image planes or multiple imaging/monitoring/therapy planes. Once the multiple image and/or monitoring and/or therapy planes are acquired, software can be employed to display the images in a variety of 3-D or two dimensional (2-D) image formats. In the therapeutic mode of operation, 3-D allows volumetric regions to be treated instead of treatments in only one plane.

The electronic or mechanical means of accessing multiple image planes id probe dependent. A 2-D array by design can electronically form 3-D image planes. A 1-D, 1.5-D, or 1.25-D array probe such as a linear array or phased array forms a single electronic image plane or slice. Therefore, sweeping the array (i.e. the image plane) through space, such as rotating it via a motor mechanism, will sweep out a volumetric image sector. Finally, a single element, annular array, or multiple-focus single element only forms a single scan line. A motor mechanism oscillates the scan line over a sector to form a 2-D image plane. Therefore, by movement of a single-element, annular array, or multiple focus transducer element in two angular directions (such as pitch and yaw motions) will sweep out a volumetric set of scan lines which can be formed into a three-dimensional image and/or used for 3-D imaging/monitoring/therapy.

Further, it should be noted that the peripheral ultrasound imaging system of the present invention may be used as a component in any other system containing a computing device that utilizes or requires ultrasound imaging and/or ultrasound imaging/monitoring/therapy as an auxiliary function.

The present invention has been described above with reference to exemplary embodiments. However, those skilled in the art having read this disclosure will recognize that changes and modifications may be made to the exemplary embodiments without departing from the scope of the present invention. These and other changes or modifications are intended to be included within the scope of the present invention, as expressed in the following claims.

We claim:

1. A peripheral ultrasound imaging system comprising:
   an ultrasound probe;
   an electronic apparatus for sending and receiving signals to and from the ultrasound probe;
   an external hardware link connecting the electronic apparatus to at least one of an unmodified personal computing device and a computing network capable of controlling and processing the signals; and
   a software program for controlling the ultrasound probe, the electronic apparatus, and the hardware link.

2. The apparatus of claim 1 wherein said hardware link forms a wireless connection between the electronic apparatus and at least one of the personal computing device and the computing network.

3. The peripheral ultrasound imaging system of claim 1 further comprising one or more additional hardware devices connected to at least one of said personal computing device and said computing network.

4. The peripheral ultrasound imaging system of claim 3 wherein said one or more additional hardware devices comprise at least one of a modem for connecting to an internet, a network card for connecting to a local area network, a printer for providing copies of displayed images, a remote storage device for storing data and software programs, and a remote unit for at least one of displaying and controlling imaging.

5. The peripheral ultrasound imaging system of claim 4 further comprising encapsulation layer software for providing a stable interface between the software program for controlling the ultrasound probe and the electronic apparatus, and each of the personal computing device, the computing network, the ultrasound probe, the hardware link, and said one or more additional hardware devices.

6. The peripheral ultrasound imaging system of claim 5 wherein said encapsulation layer software comprises:
   a set of logical device components for providing a high level interface to each of the personal computing device, the computing network, the ultrasound probe, the electronic apparatus, the hardware link, and said one or more additional hardware devices; and
   a control component for controlling communication between each of the personal computing device, the computing network, the ultrasound probe, the electronic apparatus, the hardware link, and said one or more additional hardware devices.

7. The peripheral ultrasound imaging system of claim 5 further comprising a plurality of hardware drivers for passing data between said encapsulation layer software and each of the personal computing device, the computing network, the ultrasound probe, the electronic apparatus, the hardware link, and said one or more additional hardware devices.

8. The peripheral ultrasound imaging system of claim 1 wherein said electronic apparatus comprises:
   a transmitter for transmitting signals to the ultrasound probe;
   a receiver for receiving signals from said ultrasound probe,
   a signal processor for processing signals received from the receiver,
   a real-time control for controlling the process of signals in real-time; and
   an interface logic component for providing a processed signal interface between the hardware link and at least one of the personal computing device and the computing network.

9. The peripheral ultrasound imaging system of claim 8 wherein said electronic apparatus further comprises at least one of a motor control for driving the ultrasound probe and a scan converter for converting the processed signals into a scan.

10. The peripheral ultrasound imaging system of claim 1 wherein said ultrasound probe comprises at least one of a motorized annular array probe, a motorized single element probe, a motorized multiple focus single element probe, and a transducer array.

11. The peripheral ultrasound imaging system of claim 1 wherein said software program for controlling the ultrasound probe and the electronic apparatus comprises:

a user interface for providing an interface for a user with the peripheral ultrasound imaging system through at least one of the electronic apparatus, the hardware link, the personal computing device, and the computing network;

an ultrasound system control for providing an interface for controlling the peripheral ultrasound imaging system through at least one of the personal computing device, the computer network, the ultrasound probe, the electronic apparatus, and the hardware link;

an external application interface for providing an interface for an external application through at least one of the personal computing device, the computing network, the ultrasound probe, the electronic apparatus, the hardware link and the software program for controlling the ultrasound probe and the hardware link; and an add-in support application interface for allowing an external application to be integrated into the peripheral ultrasound imaging system.

12. The peripheral ultrasound imaging system of claim 11 wherein said software program for controlling the ultrasound probe and the electronic apparatus further comprises a reporting application interface for providing a user with a hard copy of any scanned image.

13. The peripheral ultrasound imaging apparatus of claim 11 wherein said external application comprises at least one of a clinical application, a post-processing application, and a diagnostic application.

14. An electronic apparatus for connecting an ultrasound probe to at least one of a computer network and a personal computing device to create an ultrasound imaging system wherein said electronic apparatus comprises:

a transmitter for transmitting signals to the ultrasound probe.

a receiver for receiving signals from said ultrasound probe, a signal processor for processing signals received from the receiver, a real-time control for controlling the process of signals in real-time; and an interface logic component for providing a processed signal interface between the electronic apparatus and at least one of a computer network and a personal computing device.

15. The electronic apparatus of claim 14 wherein said hardware link further comprises at least one of a motor control for driving the ultrasound probe and a scan converter for converting the processed signals into a scan.

16. A method for at least one of ultrasound imaging and ultrasound therapy comprising the steps of:

providing an ultrasound probe;

providing at least one of a computer network and a personal computing device, each having means for controlling and displaying information;

connecting the ultrasound probe and at least one of the computer network and the personal computing device with an electronic apparatus having means for receiving and processing signals from the ultrasound probe and sending the processed signals to at least one of the computer network and the personal computing device;

activating said ultrasound probe; and controlling said ultrasound probe and said electronic apparatus by employing software designed to control said ultrasound probe and said electronic apparatus.

17. A 3-D peripheral ultrasound system for performing at least one of a 3-D ultrasound imaging, 3-D ultrasound monitoring, and 3-D ultrasound therapy comprising:

an ultrasound probe;

an electronic apparatus for sending and receiving signals to and from the ultrasound probe and for accessing multiple image planes from the ultrasound probe;

an external hardware link connecting the electronic apparatus to at least one of an unmodified personal computing device and a computing network capable of controlling and processing the signals and images; and a software program for controlling the ultrasound probe, the electronic apparatus, and the hardware link.

* * * * *